(12) United States Patent
Padmanaban et al.

(10) Patent No.: US 7,776,911 B2
(45) Date of Patent: Aug. 17, 2010

(54) ANTIMALARIAL DRUG CONTAINING SYNERGISTIC COMBINATION OF CURCUMIN AND ARTEMISININ

(75) Inventors: Govindarajan Padmanaban, Bangalore (IN); Pundi Narasimhan Rangarajan, Bangalore (IN); Vathsala Palakkod Govindan, Bangalore (IN); Dalavaikodihalli Nanjiah Nandakumar, Bangalore (IN); Viswanathan Arun Nagaraj, Bangalore (IN)

(73) Assignee: Indian Institute of Science, Bangalore (IN)

( * ) Notice: Subject to any disclaimer, the term of this patent is extended or adjusted under 35 U.S.C. 154(b) by 1290 days.

(21) Appl. No.: 11/268,762

(22) Filed: Nov. 7, 2005

(65) Prior Publication Data

US 2007/0105945 A1    May 10, 2007

(51) Int. Cl.
*A61K 31/35* (2006.01)
*A61K 31/12* (2006.01)

(52) U.S. Cl. ..................................... 514/453; 514/679
(58) Field of Classification Search ................. 514/453, 514/679
See application file for complete search history.

(56) References Cited

U.S. PATENT DOCUMENTS 5,129,865 A * 7/1992 Brock et al. ................. 474/152
2001/0051184 A1* 12/2001 Heng ......................... 424/461

OTHER PUBLICATIONS

Rasmussen et al. "A simple and efficient separation of the Curcumins, the antipropozoal constituents of Curcuma longa," Planta Med., 2000, vol. 66, pp. 396-398.*

* cited by examiner

*Primary Examiner*—Shengjun Wang
(74) *Attorney, Agent, or Firm*—Ladas and Parry LLP

(57) ABSTRACT

A pharmaceutical composition for the treatment of malaria in mammals is disclosed. The composition comprises of a synergistic combination of curcumin and artemisinin.

5 Claims, 4 Drawing Sheets

ANTIMALARIAL DRUG CONTAINING SYNERGISTIC COMBINATION OF CURCUMIN AND ARTEMISININ

FIELD OF INVENTION

The present invention relates to an anti malarial composition containing synergistic combination of curcumin and artemisinin. The present invention also relates to a method for the preparation of an anti malarial drug containing a synergistic combination of curcumin and artemisinin. The present invention also relates to a method for the treatment of malaria employing the novel antimalarial composition of the present invention.

BACKGROUND AND PRIOR ART

Malaria afflicts 300-500 mn people globally and 2-3 mn die every year. More than a million children die in Africa. The problem is also serious in South East Asia followed by the Indian subcontinent and South America, where economic loss due to morbidity and loss of man-hours is high.

The two major parasite species causing malaria are *Plasmodium falciparum* and *Plasmodium vivax*, although *P. ovale* and *P. malariae* are also involved, but to a minor extent. While, *P. vivax* infection is by and large treatable by antimalarial drugs, *P. falciparum* is proving to be quite difficult to treat effectively. *P. falciparum* has become resistant to the first line (chloroquine) and second line (sulfadoxine-pyrimethanine (S.P)) drugs and resistance is spreading in different continents (1,2). The roll back programme of the WHO against malaria has received a setback in view of resistance development (3,4) and this has led to a policy decision to use combination therapy with artemisinin or its derivatives as the principal component (5).

Artemisinin is a sesquiterpene endoperoxide isolated from the plant *Artemisia annua* and the plant extract has been in traditional use in China. Artemisinin, the active principle has been in use for the last 20 years in China (6,7). Artemisinin is very effective and has less side effects. However, outside of China and a few other neighboring countries, it has been used as an emergency drug and there are concerns in introducing it as a front line drug (8). First of all, it is expensive. There is not enough artemisinin available to treat all the cases globally and especially, in Africa although, attempts are underway to cultivate the plant in many countries. Artemisinin monotherapy suffers from the problem of recrudescence. Although, no resistance has so far been reported against artemisinin, wide use as front line drug can lead to improper and suboptimal use leading to development of resistance. Therefore, WHO has favoured the development of drug combinations with artemisinin or its derivatives, so that possible development of resistance to individual components in the combination is delayed and recrudescence due to artemisinin monotherapy is prevented (8).

Reference may be made to Yeung, S, Pongtavornpinyo W, Hastings, I M, Mills, A. J. and White N. J. (2004). Antimalarial drug resistance, artemisinin-based combination therapy and the contribution of modeling to elucidating policy choices. Am. J. Trop. Med. Hyg. 11, (2 suppl.), 179-186, wherein the only registered combination antimalarial with artemisinin recently made available is artemisinin-lumifantrine (co-artem, Novartis International AG, Basel, Switzerland), although efforts are underway to develop other coformulations. Co-artem is expensive, costing around US $2.4 per adult course, compared to the traditional chloroquine/SP therapy costing US $ 0.1-0.2, although efforts are underway to bring down the cost to less than US $ 1.0 (9,10).

Reference may be made to "Reddy R C, Vathsala, P G, Keshamouni V G, Padmanaban, G. and Rangarajan P N (2005) Curcumin for malaria therapy Biochem. Biophys. Res. Comm. 326, 472-474" wherein curcumin isolated from the roots of turmeric (curcumalonga) has antimalarial activity in a culture of *P. falciparum* and mice infected with *P. berghei*. Turmeric is used widely in Indian cooking and curcumin is reported to have anti-tumorigenic, anti-oxidant, anti-inflammatory and anti-microbial effects (12,13). However, turmeric has never known to be employed in practice as a drug for treatment of malaria.

Thus, in spite of the increase in incidents of the malarial parasite becoming more and more drug resistant, no prior art known to the applicant discloses an effective alternative to the present day drugs used for treatment of malaria.

Reference may be made to Trager W and Jensen B (1976). Human malaria parasites in continuous culture-Science, 193, 673-675 wherein the *P falciparum* was maintained in culture using human O+ve red cells and serum by the candle jar method as per standard protocols.

OBJECTS OF THE INVENTION

It is therefore, one of the objects of the present invention to provide a pharmaceutical composition for use in the treatment of malaria.

It is another object of the present invention to provide a pharmaceutical composition for use in the treatment of malaria to which the malarial parasites are not resistant.

It is another object of the present invention to provide a pharmaceutical composition for use in the treatment of malaria, which is not expensive and easy to manufacture.

SUMMARY OF THE INVENTION

The above and other objects of the present invention are achieved by the novel pharmaceutical composition for the treatment for the malaria comprising of an effective amount of curcumin or derivatives in combination with an effective amount of artemisinin or derivatives.

In a preferred feature, the pharmaceutical composition of the present invention may be administered to a patient as a combination.

In another preferred feature, an effective amount of curcumin or derivatives in combination with an effective amount of artemisinin or derivatives may be adminstered to a patient in need thereof together or one after another.

In a preferred feature, the pharmaceutical composition of the present invention may be administered to a patient parenterally and or orally.

In an embodiment of the present invention the effective combination may contain subcurative doses of artemisinin and its derivatives with curcumin preventing recrudescence and acting against drug-resistant malaria.

In an another embodiment of the present invention the anti malarial drug may contain synergistic combination of curcumin and artemisinin having IC 50 values for artemisinin and curcumin in the range of 45 nM-55 nM and 15-17 μM respectively.

BRIEF DESCRIPTION OF THE ACCOMPANYING DRAWINGS

The present invention will now be described with reference to the accompanying drawings wherein:

FIGS. 1(a) and (b) show the $IC_{50}$ estimation for curcumin and artemisinin respectively;

FIGS. 2(a), (b), (c) and (d) show the isobolographic analysis of artemisinin and curcumin interaction in *Plasmodium falciparum*.

DETAILED DESCRIPTION

The present invention is based on an unexpected finding that a combination drug therapy consisting of curcumin and artemisinin interact synergistically with unexpected efficacy in the treatment of malaria.

In accordance with the present invention, the drugs, curcumin and artemisinin, were added singly or in combination to 100 μl to 500 μl cultures of *P. falciparum* in triplicate using DMSO or acetone or ethanol as the solvent. Appropriate solvent controls were used. Parasite growth was measured by staining the slides with Giemsa as well as [α3H]-hypoxanthine uptake. In the latter case, the cultured cells were lysed with water and the parasites collected by filtration, washed and radioactivity measured. Adult f mice (40-50 g) were infected with *P. berghei* by intraperitoneal injection of an aliquot of infected mouse blood. After 24 hr, the animals were given a single injection of different amounts of artemisinin derivative at a dose of 5 mg/mouse. The oral feeding was repeated after 24 hr and 48 hr. Parasite count was measured in blood before and drug therapy at different time intervals using Giemsa to stain the slides. All the infected mice die in a span of 5-8 days and the efficacy of the drugs given singly or in combination was measured in terms of parasite clearance in blood and protection against mortality.

Figure 2:
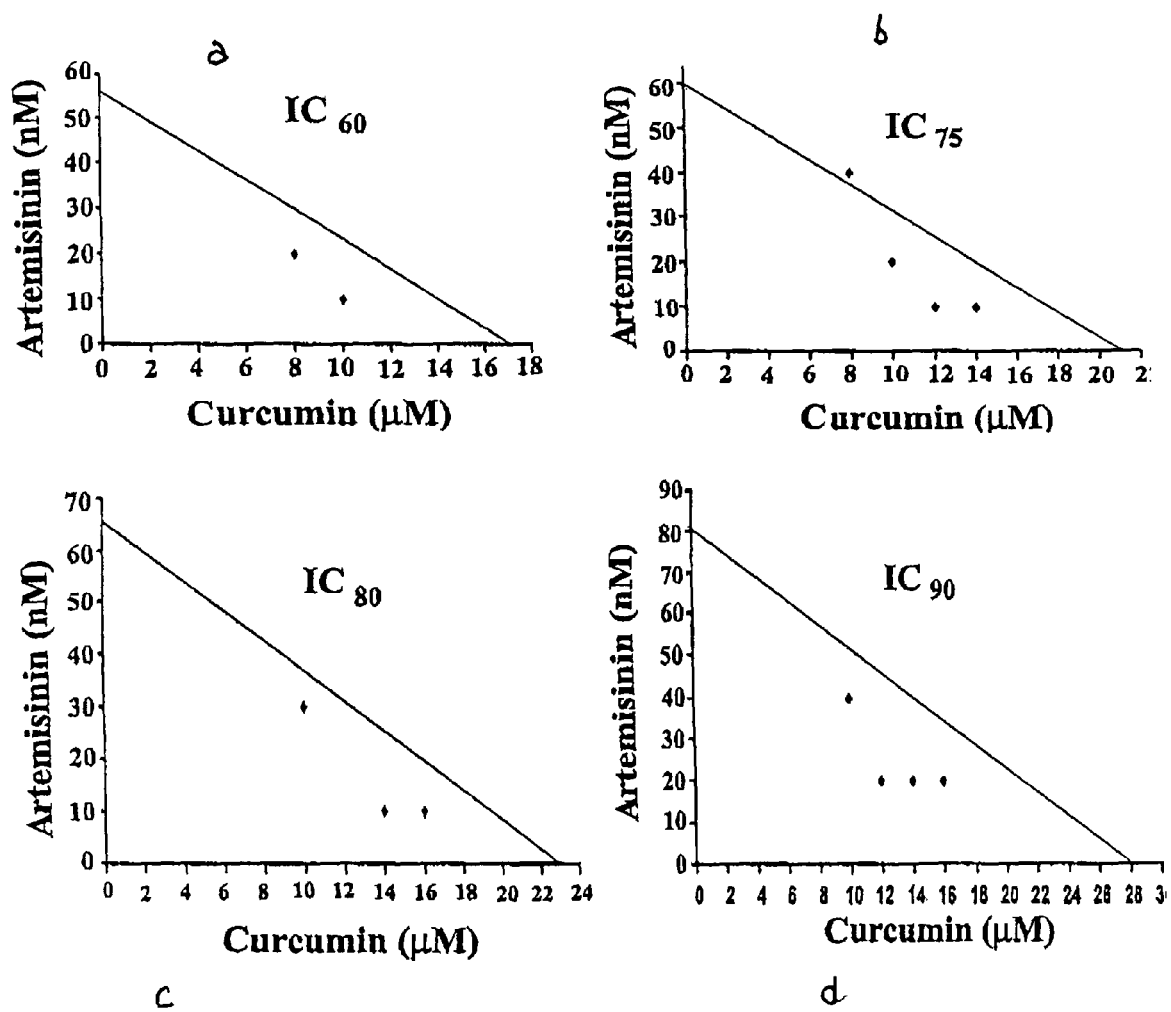

Thereafter, the efficacy of a combination of curcumin with artemisinin in *P. falciparum* culture and mice infected with *P. berghei* was tested. It was unexpectedly found that the combination extremely effective as distinguished from the individual components The results shown in FIG. 1a and 1b reveal that the IC 50 values for curcumin and artemisinin are around 15 μM and 55 nM respectively. The range in different experiments with different starting parasitemia of 2-3%, is 15-17 μM and 45-55 nM for curcumin and artemisinin respectively, using [3H] hypoxanthine uptake as a quantitative measure for growth. The potency of the combination was assessed by isobolographic characterization of the drug interactions. The additive or synergistic or antagonistic effects were assessed based on the following interaction index:

$$\frac{Ac}{AE} + \frac{Bc}{BE} = I$$

where Ac and Bc are the doses of curcumin and artemisin in combination associated with a given level of effect e.g., IC 60, IC 75, IC 80 etc., and AE and BE are the doses of individual drugs that produce the same level of effects. When I is less than 1 the drugs interact synergistically and the isobol bows below the line of additivity. When I is equal to 1 the isobol is coincident with the line of additivity and the interaction is additive. When I is greater than 1, the isobol bows above the line of additivity and the interaction is antagonistic. The results presented in FIG. 2(a-d) clearly indicate that the I values are less than 1 for different combinations of curcumin and artemisinin, the isobol falling below the line of additivity at the given level of effect namely, IC 60, IC 75, IC 80 and IC 90. The interaction between curcumin and artemisinin is thus clearly synergistic.

Figure 3:
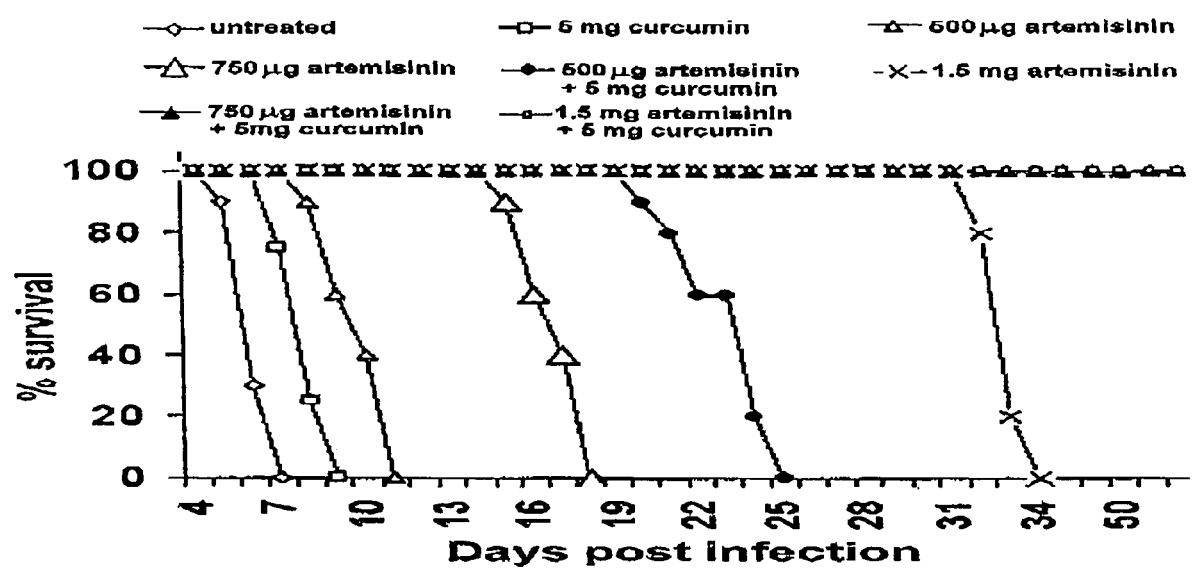
FIG. 3 shows the effect of curcumin/α-β Arteether combination treatment on protection of mice infected with *Plasmodium berghei*.
Figure 4:
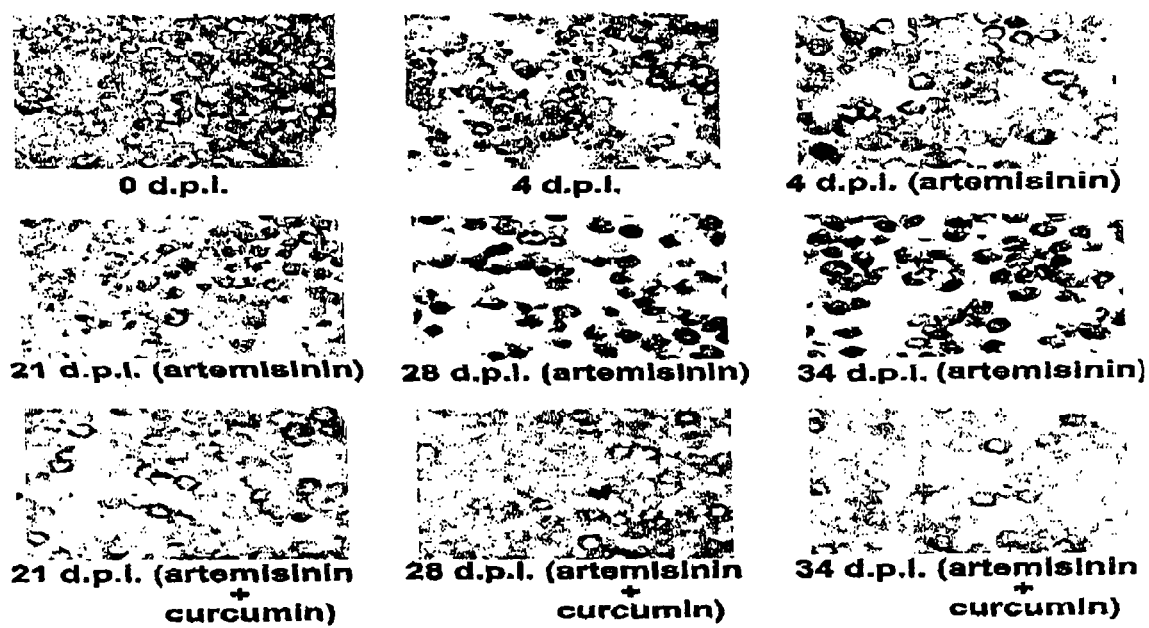
FIG. 4 shows artemisinin/curcumin combination treatment on protection of mice infected with *Plasmodium berghei*.

Encouraged by these results, in vivo experiments were carried out in mice infected with *P. berghei* as per the protocol described. Striking results were obtained in terms of parasite clearance and protection against mortality. The experiments were carried out with 6 mice per batch and the experiments were repeated at least 3 times. The results presented in FIG. 3 represent those obtained in a typical experiment. The results obtained in the $2^{nd}$ and $3^{rd}$ experiments are identical in pattern. The average pattern obtained with the infected animals is as follows. All the infected animals die in about 5-8 days. Curcumin treatment (3 day oral treatment) alone results in death in about 10-12 days. A single injection of artemisinin derivative (α,β-arteether) at a dose of 500 μg/mouse results in death of animals in 10-12 days. Oral treatment of curcumin at this dose of artemisinin derivative (500 μg/mouse) delays death and the animals die between 20-25 days. Treatment with a single injection α,β-arteether at 750 μg and 1.5 mg results in death of animals between 20-26 days and 32-38 days respectively. Interestingly, 3 day oral regimen of curcumin at these two doses of artemisinin derivative tested (750 μg and 1.5 mg) protects the animals completely and there is no mortality. The animals continue to live normally for several months. This picture is also supported by parasite load in blood (FIG. 4). A single injection of α,β-arteether clears the parasites in blood initially, but there is recrudescence and build up of parasitemia leading to death of animals at various time intervals. The effective combination doses lead to complete clearance of parasitemia correlating with protection.

The present invention will now be described with reference to the following non-limitative examples, which are given by way of illustration of the present invention and therefore, should not be construed to limit the scope of the present invention.

Example 1

Synergistic Actions of Sublethal Doses of Curcumin and Artemisinin in a Culture of *Plasmodium falciparum*

Methodology

*P. falciparum* (chloroquine-resistant) was maintained in culture using human O+ve red cells and serum by the candle jar method as per standard protocols. In accordance with the present invention, the drugs, curcumin and artemisinin, were added singly or in combination at different concentrations to 100 μl cultures of *P. falciparum* in triplicate using DMSO or acetone or ethanol as the solvent. Appropriate solvent controls were used. Parasite growth was quantitatively measured using 3[H]-hypoxanthine uptake. The cultured cells were incubated for 48 hrs and then the parasites were collected by filtration after lysis of the cells. The filters were extensively washed and then radioactivity measured. The IC 50 values for curcumin and artemisinin were individually measured. Based on these values, different combinations of curcumin and artemisinin were employed to obtain IC 60, IC 75, IC 80 and IC 90 values. The potency of the combination was assessed by isobolographic characterization of drug interactions.

Figure 1:
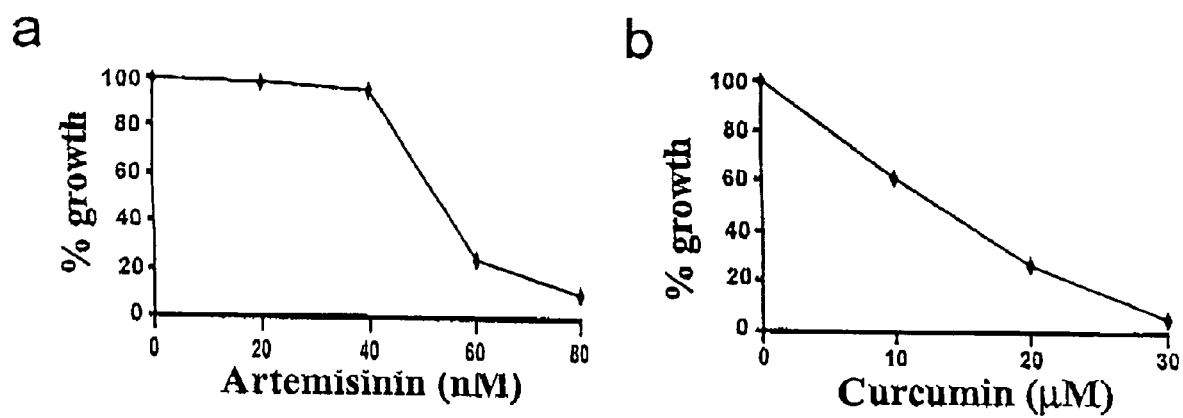

Observations:

The IC 50 values for artemisinin and curcumin were found to be between 45 nM-55 nM and 15-17 nM respectively in FIG. 1. The data obtained with the isobolographic analysis are presented in FIG. 2. At the various combinations of the two drugs used to obtain TC 60, IC 75, TC 80 and TC90 values, the isobol bows below the line of additivity. The T values were calculated from the equation.

$$1 = \frac{Ac}{AE} + \frac{Bc}{BE}$$

where Ac and Bc are the concentrations of curcumin and artemisinin in combination giving rise to the IC 60, IC 75, IC 80 and IC 90 effects and ~ ad BE are the concentrations of the individual drugs required for the same level of effects. The T values ranged from 0.7 to 0.85 in all combinations. The isobol bowling below the line of additivity and the T values being less than 1 indicate that the curcumin-artemisinin. Interaction is clearly synergistic Example 2

Synergistic Actions of Curcumin and Subcurative Doses of Artemisinin Derivatives in *P. berghei* Infected Mice Methodology; Mice (~40 g) were infected ~ with *P. berghei* by intraperitoneal infection. After 24 hrs, the animals received a single injection of different concentrations of a derivative of artemisinin (α,β-arteether) (500~g to 1.5 mg) by the intramuscular route. After 1 hr, curcumin (5 mg) in DMSO was fed orally. The oral treatment was repeated after 24 hr and 48 hr. Blood smears were made from the mice at different day intervals and parasites stained with Giemsa. The animals were observed to assess mortality and other external changes. The experiments were repeated thrice with 6 mice in each group.

Observations:

All the *P. berghei* infected mice died in about 5-8 days. The infected mice died on different days depending on the drug treatments provided as described below. Curcumin treatment (3 days oral treatment) alone resulted in death of animals between 10-12 days. A single injection α,β-arteether at 500 μg/mouse followed by a 3 day oral treatment or curcumin led-to delay of mortality and the animals died between 20-25 days. Treatment with a single injection of α,β-arteether at 750 μg and 1.5 mg per mouse resulted in the death of animals between 20-26 days and 32-38 days respectively. Interestingly, a 3 day oral regimen of curcumin at these two doses of artemisinin (single injections) led to complete protection of animals and there was no mortality. These results are presented in FIG. 3. This picture is also supported by parasite load in blood (FIG. 4). A single injection of α,β-arteether clears parasites in blood initially, but there was recrudescence and build up of parasitemia leading to death of animals at various time intervals. The effective combination doses led to complete clearance of parasitemia correlating with the protection of the animals against mortality.

The Main Advantages of the present inventions are:
1. Artemisinin and curcumin (as a constituent of turmeric) are in human use for a long time.
2. Curcumin is non-toxic and doses are high as 8 g/day for 3 months did not result in toxicity in a phase I clinical trial.
3. No resistance has been reported against curcumin or artemisinin.
4. Extrapolating the effectiveness of the combination therapy in mice at 750 Mg α,β-arteether (single parenteral dose) and 15 mg of curcumin (a total of 3 doses), the corresponding human dose would work out to 150 mg arteether/70 kg and 1.5 g/70 kg of curcumin (split into 3 doses). WHO has recommended a uniform 6 dose regimen of coartem against malaria in semi-immune and non-immune patients (20).
5. This works out to 480 mg artemisinin and 2850 mg of lumifantrine over a 3 day course of treatment. Artemisinin given as monotherapy needs a 7 day treatment at even higher doses and there is already deep concern of self medication at lower doses with potential for recrudescence and development of resistance in a few countries (8). Thus, a curcumin/artemisinin combination can lead to lower consumption of artemisinin and a decrease in the cost of the combination therapy compared to that with coartem.
6. Curcumin is very effective in preventing recrudescence due to artemisinin monotherapy.

We claim:

1. A method for treating malaria in a mammal in need thereof which comprises administering to the mammal synergistic effective amounts of curcumin and artemisinin.

2. The method as claimed in claim 1 wherein said artemisinin is employed in a dosage of about 150 mg and said curcumin is employed in a dosage of about 1.5 g divided into three equal doses.

3. The method as claimed in claim 1 wherein said curcumin prevents recrudescence and acts against drug-resistant malaria.

4. The method according to claim 1 wherein the malaria is caused by *P. falciparum*.

5. The method according to claim 1 wherein the malaria is caused by *P. berghei*.

* * * * *